US007608626B2

(12) United States Patent (10) Patent No.: US 7,608,626 B2
Sabb et al. (45) Date of Patent: Oct. 27, 2009

(54) SUBSTITUTED INDOLIZINES AND DERIVATIVES AS CNS AGENTS

(75) Inventors: Annmarie Louise Sabb, Pennington, NJ (US); Robert Lewis Vogel, Collingswood, NJ (US)

(73) Assignee: Wyeth, Madison, NJ (US)

( * ) Notice: Subject to any disclaimer, the term of this patent is extended or adjusted under 35 U.S.C. 154(b) by 201 days.

(21) Appl. No.: 11/260,716

(22) Filed: Oct. 27, 2005

(65) Prior Publication Data

US 2006/0094752 A1 May 4, 2006

Related U.S. Application Data

(60) Provisional application No. 60/624,423, filed on Nov. 1, 2004.

(51) Int. Cl.
C07D 221/02 (2006.01)
A01N 43/42 (2006.01)
A61K 31/44 (2006.01)

(52) U.S. Cl. .................................. 514/299; 546/112
(58) Field of Classification Search ................ 514/299; 546/112
See application file for complete search history.

(56) References Cited

U.S. PATENT DOCUMENTS

| 2002/0002749 A1 | 1/2002 | Breton et al. ............... 8/405 |
| 2003/0134843 A1 | 7/2003 | Lubisch et al. ......... 514/217.07 |

FOREIGN PATENT DOCUMENTS

| DE | 19907701 A1 | 8/2000 |
| EP | 0 213 696 A2 | 3/1987 |
| EP | 0 252 643 A1 | 1/1988 |
| EP | 0 279 125 A1 | 8/1988 |
| EP | 0 167 901 B1 | 4/1990 |
| EP | 0 213 696 B1 | 1/1991 |
| EP | 0 279 125 B1 | 4/1992 |
| EP | 1129691 * | 5/2001 |
| EP | 0 950 661 B1 | 11/2003 |
| WO | 92/21678 A1 | 12/1992 |
| WO | 95/04737 A1 | 2/1995 |
| WO | 95/07279 A2 | 3/1995 |
| WO | 97/11074 A1 | 3/1997 |
| WO | 00/06564 A1 | 2/2000 |
| WO | 00/12510 A1 | 3/2000 |
| WO | 00/34242 A1 | 6/2000 |
| WO | 01/05789 A1 | 1/2001 |
| WO | 01/74814 A1 | 10/2001 |
| WO | 02/051844 A1 | 7/2002 |

OTHER PUBLICATIONS

Marazziti et al., Neurochemistry International, vol. 42, 2003, pp. 511-516.*
Cingolani et al., European Journal of medicinal chemistry, 1988, vol. 23, pp. 291-294.*
Cingolani et al., European Journal of medicinal chemistry, 1990, vol. 25, pp. 709-712.*
Ames, D. E. et al., "The preparation of aminoalkylpyrrocolines," *Journal of The Chemical Society*, Chemical Society. Letchworth, GB, 1959, pp. 620-622, XP-002083697.
Cingolani, G. M. et al., "Indolizine derivatives with biological activity V. 1-(2-Aminoethyl)-2-methylindolizine and its N-alkyl derivatives," *Eur. J. Med. Chem.*, 1988, 23(3), 291-294, XP-002378332.
Walter, L. A. et al., "2-Phenylindolizines," *Journal of Medicinal Chemistry*, 1967, 10(3), 498-499.
Allison, D. B. et al., "Antipsychotic-Induced Weight Gain: A Comprehensive Research Synthesis," *Am. J. Psychiatry*, 1999, 156, 1686-1696.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4), 285-298.
Bundgaard, H., "Means to enhance penetration; Prodrugs as a means to improve the delivery of peptide drugs," *Advanced Drug Deliver Reviews*, 1992, 8, 1-38.
CAS Registry 101350-38-3, Apr. 5, 1986.
Cingolani, G. M. et al., "Indolizine derivatives with biological activity VI 1-(2-aminoethyl)-3-benzyl-7-methoxy-2-methylindolizine, benanserin structural analogue," *Eur. J. Med. Chem.*, 1990, 25, 709-712.
Cowen, P. J. et al., "Hypophagic, Endocrine and Subjective Responses to m-Chlorophenylpiperazine in Healthy Men and Women," *Human Psychopharmacology*, 1995, 10, 385-391.

(Continued)

*Primary Examiner*—Janet L Andres
*Assistant Examiner*—Niloofar Rahmani
(74) *Attorney, Agent, or Firm*—Feldman Gale, P.A.; David A. Cherry

(57) ABSTRACT

Compounds of formula 1 or pharmaceutically acceptable salts thereof are provided:

(1)

[Chemical structure showing indolizine core with substituents $R^1$, $R^2$, $R^3$, $R^4$, $R^5$, $R^6$, $R^7$, and an aminoethyl group with $R^8$ and $R$ on the nitrogen]

which are agonists or partial agonists of the 2C subtype of brain serotonin receptors. The compounds, and compositions containing the compounds, can be used to treat a variety of central nervous system disorders such as schizophrenia.

21 Claims, No Drawings

OTHER PUBLICATIONS

Dalton, L.K. et al., "Synthesis of Benz[b]indolizines and related Compounds," *Aust. J. Chem.* 1969 22, 1525-1530.

Di Giovanni, G. et al., "Preferential Modulation of Mesolimbic Vs. Nigrostriatal Dopaminergic Function by Serotonin$_{2C/2B}$ Receptor Agonists: A Combined In Vivo Electrophysiological and Microdialysis Study," *Synapse*, 2000, 35, 53-61.

Di Matteo, V. et al., "SB 242 084, a selective serotonin$_{2C}$ receptor antagonist, increases dopaminergic transmissions in the mesolimbic system," *Nueropharmacology*, 1999, 38, 1195-1205.

Di Matteo, V. et al., "Selective blockade of serotonin$_{2C/2B}$ receptors enhances dopamine release in the rat nucleus accumbens," *Nueropharmacology*, 1998, 37, 265-272.

Eliel, E. L., *Stereochemistry of Carbon Compounds*, McGraw Hill, NY (1962) Ch. 4, pp. 46-87.

Fox, S. H. et al., "Behavioral Effects of 5-HT$_{2C}$ Receptor Antagonism in the Substantia Nigra Zona Reticulata of the 6-Hydroxydopamine-Lesioned Rat Model of Parkinson's Disease," *Experimental Neurology*, 1998, 151, 35-49.

Higuchi and Stella (eds.), *Prodrugs as Novel Drug Delivery Systems*, American Chemical Society (1975), pp. 1-115 and 196-223.

Jacques, J. et al., *Enantiomers, Racemates and Resolutions*, Wiley Interscience, NY (1981) pp. 251-434.

Krogsgaard-Larsen, et al., (ed). *Design and Application of Prodrugs, Textbook of Drug Design and Development*, Chapter 5, 113-191, 1991.

Lowry, O. H. et al., "Protein Measurement With The Folin Phenol Reagent," *J. Biol. Chem.*, 1951, 193, 265-275.

Masand, P. S., "Weight gain associated with psychotropic drugs," *Exp. Opin. Pharmacother.*, 2000, 1, 377-389.

Millan, M. J. et al., "Serotonin (5-HT)$_{2C}$ receptors tonically inhibit dopamine (DA) and noradrenaline (NA), but not 5-HT, release in the frontal cortex in vivo," *Neuropharmacology*, 1998, 37, 953-955.

*Remington's Pharmaceutical Sciences*, 17$^{th}$ Ed., Gennaro, A. R. (Ed.), Mack Publishing Company, Easton, PA (1985) pp. 1409-1677.

Rosenzweig-Lipson, S. et al., "Antiobesity-like effects of the selective 5-HT2C Agonist Way-161503," *ASPET Abstract and Poster*, 2000.

Schotte, A. et al., "Risperidone compared with new and reference antipsychotic drugs: in vitro and in vivo receptor binding," *Psychopharmacology*, 1996, 124, 57-73.

Uchida, T. et al., "Methods for the Construction of the Indolizine Nucleus", *Synthesis* 1976, 209-236.

Whitaker, R., "Atypical Antipsychotics: A Modest Advance in Treating Schizophrenia," Spectrum Life Sciences. *Decision Resources*, Feb. 11, 2000, 2-1 to 2-12.

Widder, et al. (ed.), *Methods in Enzymology*, vol. 112, Academic Press (1985), pp. 309-396.

Wilen, S.H. *Tables of Resolving Agents and Optical Resolutions*, pp. 268-298, E.L. Eliel, Ed., University of Notre Dame Press, Notre Dame, IN 1972.

Wilen, S.H., et al., "Strategies in optical resolutions," *Tetrahedron*, 1977, 33, 2725- 2736.

\* cited by examiner

SUBSTITUTED INDOLIZINES AND DERIVATIVES AS CNS AGENTS

CROSS REFERENCE TO RELATED APPLICATIONS

This application claims priority of U.S. Provisional Application Ser. No. 60/624,423, filed Nov. 1, 2004, the disclosure of which is incorporated herein by reference in its entirety for all purposes.

FIELD OF THE INVENTION

The present invention relates to novel indolizin-1-yl derivatives that act as agonists or partial agonists of the 5-$HT_{2C}$ receptor, processes for their preparation, and their use in medicine.

BACKGROUND OF THE INVENTION

Schizophrenia affects approximately 5 million people. At present, the most widespread treatments for schizophrenia are the 'atypical' antipsychotics, which combine dopamine (D2) receptor antagonism with serotonin (5-$HT_{2A}$) receptor antagonism. Despite the reported advances in efficacy and side-effect liability of atypical antipsychotics over typical antipsychotics, these compounds do not adequately treat all of the symptoms of schizophrenia and are accompanied by problematic side effects including weight gain (Allison, D. B., et. al., *Am. J. Psychiatry*, 156: 1686-1696, 1999; Masand, P. S., *Exp. Opin. Pharmacother*. I: 377-389, 2000; Whitaker, R., Spectrum Life Sciences. Decision Resources. 2:1-9, 2000). Novel antipsychotics that are effective in treating the mood disorders or the cognitive impairments in schizophrenia without producing weight gain would represent a significant advance in the treatment of schizophrenia.

5-$HT_{2C}$ agonists represent a novel therapeutic approach toward the treatment of schizophrenia. Several lines of evidence support a role for 5-$HT_{2C}$ receptor agonism as a treatment for schizophrenia. Studies with 5-$HT_{2C}$ antagonists suggest that these compounds increase synaptic levels of dopamine and may be effective in animal models of Parkinson's disease (Di Matteo, V., et. al., *Neuropharmacology* 37: 265-272, 1998; Fox, S. H., et. al., *Experimental Neurology* 151: 35-49, 1998). Since the positive symptoms of schizophrenia are associated with increased levels of dopamine, compounds with actions opposite those of 5-$HT_{2C}$ antagonists such as 5-$HT_{2C}$ agonists should reduce levels of synaptic dopamine. Recent studies have demonstrated that 5-$HT_{2C}$ agonists decrease levels of dopamine in the prefrontal cortex and nucleus accumbens (Millan, M. J., et. al., *Neuropharmacology* 37: 953-955, 1998; Di Matteo, V., et. al., *Neuropharmacology* 38: 1195-1205, 1999; Di Giovanni, G., et. al., *Synapse* 35: 53-61, 2000), brain regions that are thought to mediate critical antipsychotic effects of drugs like clozapine. In contrast, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in substantia nigra (Di Matteo and Di Giovanni, op. cit.). The differential effects of 5-$HT_{2C}$ agonists in the mesolimbic pathway relative to the nigrostriatal pathway suggests that 5-$HT_{2C}$ agonists will have limbic selectivity and will be less likely to produce extrapyramidal side effects associated with typical antipsychotics.

Atypical antipsychotics bind with high affinity to 5-$HT_{2C}$ receptors and function as 5-$HT_{2C}$ receptor antagonists or inverse agonists. Weight gain is a problematic side effect associated with atypical antipsychotics such as clozapine and olanzapine and it has been suggested that 5-$HT_{2C}$ antagonism is responsible for the increased weight gain. Conversely, stimulation of the 5-$HT_{2C}$ receptor is known to result in decreased food intake and body weight (Walsh et. al., *Psychopharmacology* 124: 57-73, 1996; Cowen, P. J., et. al., *Human Psychopharmacology* 10: 385-391, 1995; Rosenzweig-Lipson, S., et. al., ASPET abstract, 2000). As a result, 5-$HT_{2C}$ agonists will be less likely to produce the body weight increases associated with current atypical antipsychotics. Indeed, 5-$HT_{2C}$ agonists are of great interest for the treatment of obesity, a medical disorder characterized by an excess of body fat or adipose tissue and associated with such comorbidities as Type II diabetes, cardiovascular disease, hypertension, hyperlipidemia, stroke, osteoarthritis, sleep apnea, gall bladder disease, gout, some cancers, some infertility, and early mortality. Other therapeutic indications for 5-$HT_{2C}$ agonists are obsessive compulsive disorder, depression, panic disorder, sleep disorders, eating disorders and epilepsy.

SUMMARY OF THE INVENTION

The present invention relates to certain indolizin-1-yl derivatives and to their use in medicine. In one aspect, the invention relates to indolizin-1-yl derivatives that act as agonists or partial agonists of the 5-$HT_{2C}$ receptor. The compounds can be used, for example, to treat schizophrenia and the concomitant mood disorders and cognitive impairments of schizophrenia. Compounds of the present invention are preferably less likely to produce the body weight increases associated with current atypical antipsychotics. The compounds of the present invention can also be used for the treatment of obesity and its comorbidities.

In certain embodiments, the invention relates to compounds of formula 1:

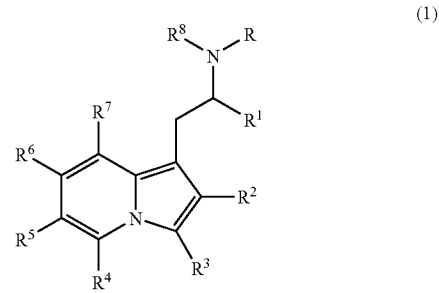

(1)

or pharmaceutically acceptable salts thereof;

wherein

R is H, $C_1$-$C_6$ alkyl, $C_5$-$C_{10}$ aryl, 5 to 10 membered heteroaryl having 1 to 3 heteroatoms each independently selected from nitrogen, oxygen or sulfur, or —C(O)R', wherein R' is $C_1$-$C_6$ alkyl, $C_5$-$C_{10}$ aryl, or 5 to 10 membered heteroaryl having 1 to 3 heteroatoms each independently selected from nitrogen, oxygen or sulfur;

$R^1$ is H, $C_1$-$C_6$ alkyl, $C_3$-$C_8$ cycloalkyl, or $C_1$-$C_6$ fluoroalkyl;

$R^2$ is $C_1$-$C_6$ alkyl, $C_3$-$C_8$ cycloalkyl, $C_1$-$C_6$ fluoroalkyl, $C_5$-$C_{10}$ aryl, or 5 to 10 membered heteroaryl having 1 to 3 heteroatoms each independently selected from nitrogen, oxygen or sulfur;

$R^3$ is H, $C_1$-$C_6$ alkyl, $C_1$-$C_6$ alkyl-$C_3$-$C_8$ cycloalkyl, or $C_1$-$C_6$ fluoroalkyl;

or alternatively $R^2$ and $R^3$ can be taken together with the carbon atoms to which they are attached to form a ring of 5-8 carbon atoms;

$R^4$, $R^5$, $R^6$, and $R^7$ are each independently H, halogen, cyano, hydroxyl, carboxyl, $C_1$-$C_6$ alkyl, $C_1$-$C_6$ fluoroalkyl, $C_1$-$C_6$ alkoxy, $C_1$-$C_6$ fluoroalkoxy, $C_5$-$C_{10}$ aryl, $C_5$-$C_{10}$ aryloxy, 5 to 10 membered heteroaryl having 1 to 3 heteroatoms each independently selected from nitrogen, oxygen or sulfur, $C_2$-$C_8$ alkenyl, $C_2$-$C_6$ alkanoyl, $C_2$-$C_6$ alkanoyloxy, $C_2$-$C_6$ alkoxycarbonyl, carboxamido, $C_2$-$C_6$ alkanamido, $C_1$-$C_6$ alkanesulfonamido, amino, $C_1$-$C_6$ monoalkylamino, dialkylamino of 1 to 6 carbon atoms per alkyl moiety, $C_3$-$C_8$ cycloalkyl, or a 3 to 8 membered heterocycloalkyl having 1 to 3 heteroatoms each independently selected from nitrogen, oxygen or sulfur;

$R^8$ is H, $C_1$-$C_6$ alkyl, $C_3$-$C_8$ cycloalkyl, or $C_5$-$C_{10}$ aryl;

wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, $C_1$-$C_6$ alkyl, $C_1$-$C_6$ fluoroalkyl, $C_1$-$C_6$ alkoxy, or $C_1$-$C_6$ fluoroalkoxy.

In certain other embodiments, the invention relates to methods for treating a patient suffering from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, substance abuse, addiction to alcohol and various other drugs, including cocaine and nicotine, sexual dysfunction, gastrointestinal disorders, obesity, or a central nervous system deficiency associated with trauma, stroke, or spinal cord injury that includes administering to the patient an effective amount of a compound of formula 1, or a pharmaceutically acceptable salt thereof.

In still other embodiments, the invention relates to compositions comprising a compound of formula 1 or a pharmaceutically acceptable salt thereof, and one or more pharmaceutically acceptable carrier.

DETAILED DESCRIPTION OF ILLUSTRITIVE EMBODIMENTS

The present invention relates to novel indolizin-1-yl derivatives that are agonists or partial agonists of the 2c subtype of brain serotonin receptors ($5HT_{2C}$).

The term "alkyl," as used herein, refers to an aliphatic hydrocarbon chain having up to 8 carbon atoms, preferably 1 to 6 carbon atoms, and more preferably 1 to 4 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. The term "lower alkyl" refers to an alkyl group having 1 to 3 carbon atoms.

The term "alkenyl," as used herein refers to an aliphatic straight or branched hydrocarbon chain having 2 to 8 carbon atoms that may contain 1 to 3 double bonds. Examples of alkenyl groups include vinyl, prop-1-enyl, allyl, methallyl, but-1-enyl, but-2-enyl, but-3-enyl, or 3,3-dimethylbut-1-enyl. In some embodiments, the alkenyl is preferably a branched alkenyl of 3 to 8 carbon atoms.

The term "cycloalkyl," as used herein, refers to a saturated or partially saturated, hydrocarbon ring containing 3 to 8 carbon atoms and more preferably 5 to 7 carbon atoms. Cycloalkyl groups may be monocyclic or bicyclic, and more preferably monocyclic. Bicyclic cycloalkyl groups are preferably bridged. "Bridged" refers to a cycloalkyl group that contains at least one carbon-carbon bond between two non-adjacent carbon atoms of the cycloalkyl ring. "Partially saturated" refers to a nonaromatic cycloalkyl group containing at least one double bond and preferably one double bond. Preferably, the cycloalkyl group is saturated. The cycloalkyl group may be unsubstituted or substituted as described hereinafter.

The term "heterocycloalkyl," as used herein, refers to a 3 to 8 membered, and more preferably 5 to 7 membered cycloalkyl group in which one to three carbon atoms of the cycloalkyl group are replaced with a heteroatom independently selected from oxygen, nitrogen, or sulfur. The heterocycloalkyl group may be saturated or partially saturated, and may be monocyclic or bicyclic (such as bridged). Preferably, the heterocycloalkyl is monocyclic. The heterocycloalkyl group may be unsubstituted or substituted as described hereinafter. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, piperadinyl, and imidazolidinyl.

The term "aryl," as used herein refers to a 5 to 10 membered carbocyclic aromatic ring. The aryl may be monocyclic or bicyclic, and may be substituted or unsubstituted. Monocyclic aryl groups preferably have 5, 6, or 7 members and bicyclic aryl groups preferably have 8, 9 or 10 members. Exemplary aryl groups include phenyl and naphthyl.

The term "aryloxy," as used herein, refers to the group Ar—O—, where Ar is an aryl group of 5 to 10 carbon atoms as previously described.

The term "heteroaryl," as used herein, refers to a 5 to 10 membered monocyclic or bicyclic carbon containing aromatic ring having 1 to 3 of its ring members independently selected from nitrogen, sulfur or oxygen. Monocyclic rings preferably have 5 to 6 members and bicyclic rings preferably have 8 to 10 membered ring structures. The heteroaryl group may be unsubstituted or substituted as described hereinafter. Examples of heteroaryls include, but are not limited to, thienyl, furyl, pyrrolyl, imidazolyl, pyrazolyl, oxazolyl, isoxazolyl, thiazolyl, isothiazolyl, pyridyl, pyrazinyl, pyrimidinyl, pyridazinyl, indolyl, indazolyl, benzofuranyl, isobenzofuranyl, benzothienyl, isobenzothienyl, quinolyl, isoquinolyl, quinoxalinyl, or quinazolinyl.

The term "fluoroalkyl," as used herein, refers to a straight or branched aliphatic hydrocarbon chain of 1 to 6 carbon atoms and preferably 1 to 3 carbon atoms, in which at least one of the hydrogen atoms is replaced with fluorine. A fluoroalkyl in which all of the hydrogen atoms have been replaced with fluorine is referred to as a "perfluoroalkyl."

The term "alkanamido," as used herein, refers to the group R—C(=O)—NH— where R is an alkyl group of 1 to 5 carbon atoms.

The term "alkanoyl," as used herein, refers to the group R—C(=O)— where R is an alkyl group of 1 to 5 carbon atoms.

The term "alkanoyloxy," as used herein, refers to the group R—C(=O)—O— where R is an alkyl group of 1 to 5 carbon atoms.

The term "alkanesulfonamido," as used herein, refers to the group R—S(O)$_2$—NH— where R is an alkyl group of 1 to 6 carbon atoms.

The term "alkoxy," as used herein, refers to the group R—O— where R is an alkyl group of 1 to 6 carbon atoms.

The term "fluoroalkoxy," as used herein, refers to the group R—O where R is a fluoroalkyl group of 1 to 6 carbon atoms. A fluoroalkoxy in which all of the hydrogen atoms have been replaced with fluorine is referred to as a "perfluoroalkoxy."

The terms "monoalkylamino" and "dialkylamino," as used herein, respectively refer to —NHR and —NRR$_a$, where R and R$_a$ are independently selected from an alkyl group of 1 to 6 carbon atoms.

The term "carboxamido," as used herein, refers to the group NH$_2$—C(=O)—.

The term "alkoxycarbonyl," as used herein, refers to the group R—O—C(=O)— where R is an alkyl group of 1 to 5 carbon atoms.

The term "carboxyl," as used herein, refers to the group —COOH.

The terms "halogen" or "halo," as used herein, refer to chlorine, bromine, fluorine or iodine.

The term "substituted," as used herein, refers to a moiety, such as an aryl, heteroaryl, cycloalkyl or heterocycloalkyl moiety having from 1 to about 5 substituents, and more preferably from 1 to about 3 substituents independently selected from a halogen, hydroxyl, alkyl of 1 to 6 carbon atoms, fluoroalkyl of 1 to 6 carbon atoms, alkoxy of 1 to 6 carbon atoms, or fluoroalkoxy of 1 to 6 carbon atoms. Preferred substituents are a halogen atom, a lower alkyl, a perfluoroalkyl of 1 to 3 carbon atoms, an alkoxy group of 1 to 3 carbon atoms or a perfluoroalkoxy of 1 to 3 carbon atoms.

The term "effective amount," as used herein, refer to the amount of a compound of formula 1 that, when administered to a patient, is effective to at least partially treat a condition from which the patient is suffering from. Such conditions include, but are not limited to, schizophrenia, schizoaffective disorder, schizophreniform disorder, L-DOPA-induced psychosis, bipolar disorder, obesity, obsessive compulsive disorder, depression, panic disorder, sleep disorders, eating disorders, and epilepsy.

The term "pharmaceutically acceptable salts" or "pharmaceutically acceptable salt" refers to salts derived from treating a compound of formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids.

The term "patient," as used herein, refers to a mammal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" or "treating," as used herein, refers to partially or completely alleviating, inhibiting, preventing, ameliorating and/or relieving the condition.

The terms "suffer" or "suffering" as used herein refers to one or more conditions that a patient has been diagnosed with, or is suspected to have.

In certain embodiments, the invention relates to compounds of formula 1:

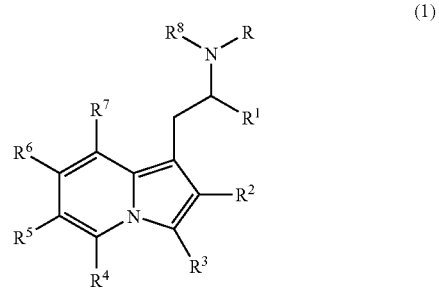

or pharmaceutically acceptable salts thereof;

wherein

R is H, $C_1$-$C_6$ alkyl, $C_5$-$C_{10}$ aryl, 5 to 10 membered heteroaryl having 1 to 3 heteroatoms each independently selected from nitrogen, oxygen or sulfur, or —C(O)R', wherein R' is $C_1$-$C_6$ alkyl, $C_5$-$C_{10}$ aryl, or 5 to 10 membered heteroaryl having 1 to 3 heteroatoms each independently selected from nitrogen, oxygen or sulfur;

$R^1$ is H, $C_1$-$C_6$ alkyl, $C_3$-$C_7$ cycloalkyl, or $C_1$-$C_6$ fluoroalkyl;

$R^2$ is $C_1$-$C_6$ alkyl, $C_3$-$C_8$ cycloalkyl, $C_1$-$C_6$ fluoroalkyl, $C_5$-$C_{10}$ aryl, or 5 to 10 membered heteroaryl having 1 to 3 heteroatoms each independently selected from nitrogen, oxygen or sulfur;

$R^3$ is H, $C_1$-$C_6$ alkyl, $C_1$-$C_6$ alkyl-$C_3$-$C_8$ cycloalkyl, or $C_1$-$C_6$ fluoroalkyl;

or alternatively $R^2$ and $R^3$ can be taken together to form a ring of 5-8 carbon atoms;

$R^4$, $R^5$, $R^6$, and $R^7$ are each independently hydrogen, halogen, cyano, hydroxyl, carboxyl, $C_1$-$C_6$ alkyl, $C_1$-$C_6$ fluoroalkyl, $C_1$-$C_6$ alkoxy, $C_1$-$C_6$ fluoroalkoxy, $C_5$-$C_{10}$ aryl, $C_5$-$C_{10}$ aryloxy, 5 to 10 membered heteroaryl having 1 to 3 heteroatoms each independently selected from nitrogen, oxygen or sulfur, $C_2$-$C_8$ alkenyl, $C_2$-$C_6$ alkanoyl, $C_2$-$C_6$ alkanoyloxy, $C_2$-$C_6$ alkoxycarbonyl, carboxamido, $C_2$-$C_6$ alkanamido, $C_1$-$C_6$ alkanesulfonamido, amino, $C_1$-$C_6$ monoalkylamino, dialkylamino of 1 to 6 carbon atoms per alkyl moiety, $C_3$-$C_8$ cycloalkyl, or a 3 to 8 membered heterocycloalkyl having 1 to 3 heteroatoms each independently selected from nitrogen, oxygen or sulfur;

$R^8$ is H, $C_1$-$C_6$ alkyl, $C_3$-$C_8$ cycloalkyl, or $C_5$-$C_{10}$ aryl;

wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, $C_1$-$C_6$ alkyl, $C_1$-$C_6$ fluoroalkyl, $C_1$-$C_6$ alkoxy, or $C_1$-$C_6$ fluoroalkoxy.

In preferred embodiments, one or more of R, $R^1$, $R^3$, and $R^8$ are independently selected from H and $C_1$-$C_6$ alkyl. In certain embodiments, R, $R^1$, $R^3$, and $R^8$ are each independently selected from H and $C_1$-$C_6$ alkyl. In certain other embodiments one, two, three, or all four of R, $R^1$, $R^3$, and $R^8$ are H.

In other preferred embodiments $R^2$ is selected from optionally substituted $C_5$ to $C_{10}$ aryl and $C_1$-$C_6$ alkyl, and more preferably an optionally substituted phenyl and lower alkyl. In certain embodiments, R, $R^1$, $R^3$, and $R^8$ are each independently selected from H and $C_1$-$C_6$ alkyl, and $R^2$ is selected from an optionally substituted $C_5$ to $C_{10}$ aryl and $C_1$-$C_6$ alkyl, and more preferably an optionally substituted phenyl and lower alkyl.

In another preferred embodiment, $R^2$ and $R^3$ are taken together to form a ring of 5-8 carbon atoms, and more preferably a ring of 5 to 6 carbon atoms. Preferred compounds in this embodiment are those in which R and $R^1$ are each independently selected from H and $C_1$-$C_6$ alkyl, and $R^4$ through $R^8$ are H.

In further preferred embodiments, $R^4$, $R^5$, $R^6$, and $R^7$ are each independently selected from H, halogen, $C_1$ to $C_6$ alkyl, $C_1$ to $C_3$ fluoroalkyl, $C_1$ to $C_3$ alkoxy, and $C_2$ to $C_8$ alkenyl. More preferably, $R^4$, $R^5$, $R^6$, and $R^7$ are each independently selected from H, halogen, and $C_1$ to $C_6$ alkyl. Even more preferably, $R^4$, $R^5$, $R^6$, and $R^7$ are each H.

In still further preferred embodiments of the invention, the compounds of formula 1 are selected from:
2-(2-phenylindolizin-1-yl)ethylamine;
2-(3-ethyl-2-phenylindolizin-1-yl)ethylamine;
2-(2-phenyl-3-propylindolizin-1-yl)ethylamine;
2-(2-ethylindolizin-1-yl)ethylamine;
2-(2,3-diethylindolizin-1-yl)ethylamine;
N-[2-(2,3-diethylindolizin-1-yl)ethyl]-N-ethylamine;
2-(2-ethyl-3-propylindolizin-1-yl)ethylamine;
N-[2-(2-ethyl-3-propylindolizin-1-yl)ethyl]-N-propylamine;
2-(2-ethyl-3-propylindolizin-1-yl)-1-methylethylamine;
1-(2-methyl-3-propylindolizin-1-yl)propan-2-amine;
1-(2-methyl-3-propylindolizin-1-yl)butan-2-amine; and
2-(1,2,3,4-tetrahydropyrido[1,2-a]indol-10-yl)ethylamine.

The compounds of formula 1 have affinity for and agonist or partial agonist activity at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorders with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the DIAGNOSTIC AND STATISTICAL MANUAL OF MENTAL DISORDERS, 4th edition, Washington, D.C., American Psychiatric Association (1994), incorporated herein by reference in its entirety.

The compounds of formula 1 are also of interest for the treatment of epilepsy; migraines; substance abuse and addiction to alcohol and various other drugs, including cocaine and nicotine; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality.

The compounds of formula 1 can also be used to treat central nervous system deficiencies associated, for example, with trauma, stroke, and spinal cord injuries. The compounds of formula 1 can therefore be used to improve or inhibit further degradation of central nervous system activity during or following the malady or trauma in question. Included in these improvements are maintenance or improvement in motor and motility skills, control, coordination, and strength.

In certain embodiments, the present invention therefore provides methods of treating, each of the conditions listed above in a patient, preferably in a human, the methods including administering an effective amount of at least one compound of formula 1 or a pharmaceutically acceptable salt thereof to a patient suffering from such a condition.

In other embodiments, the invention relates to compositions comprising at least one compound of formula 1, or a pharmaceutically acceptable salt thereof, and one or more pharmaceutically acceptable carrier. Such compositions include pharmaceutical compositions for treating or controlling disease states or conditions of the central nervous system. In certain embodiments, the compositions comprise mixtures of one or more compounds of formula 1.

Certain of the compounds of formula 1 contain stereogenic carbon atoms or other chiral elements and thus give rise to stereoisomers, including enantiomers and diastereomers. Although the stereochemistry is not shown in formula 1, formula 1 includes all of the stereoisomers of the indolizin-1-yl derivatives, as well as mixtures of the stereoisomers. Throughout this application, the name of the product, where the absolute configuration of an asymmetric center is not indicated, is intended to embrace the individual stereoisomers as well as mixtures of stereoisomers. When it is necessary to distinguish the enantiomers from one another and from the racemate, the sign of the optical rotation [(+), (−) and (±)] is utilized. Furthermore, throughout this application, the designations R* and S* are used to indicate relative stereochemistry, employing the Chemical Abstracts convention which automatically assigns R* to the lowest numbered asymmetric center.

Where an enantiomer is preferred, it may, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., *Tetrahedron* 33:2725 (1977); Eliel, E. L., Stereochemistry of Carbon Compounds (McGraw-Hill, NY, 1962); and Wilen, S. H., Tables of Resolving Agents and Optical Resolutions p. 268

(E. L. Eliel, Ed., Univ. of Notre Dame Press, Notre Dame, Ind. 1972), each of which is hereby incorporated by reference in its entirety.

The compounds of this invention can be prepared, for example, according to Schemes 1, 2, and 3.

Variables used are as defined for Formula 1, unless otherwise noted. X is halogen. R" is hydrogen or straight chain or branched alkyl of 1-6 carbon atoms, cycloalkyl of 3-7 carbon atoms, fluoroalkyl, or fluoroalkoxy.

In Scheme 1, the indolizine ring system shown is prepared by heating a substituted or unsubstituted 2-methylpyridine with a substituted or unsubstituted halomethylketone, such as bromoacetophenone, in an organic solvent, such as acetone or ethanol, followed by reaction of the pyridinium intermediate with a mild base, such as sodium bicarbonate, to give the desired 2-substituted indolizine. [Uchida, T; Matsumoto, T. "Methods for Construction of the Indolizine Nucleus", *Synthesis* 1976, 209-236.] Acylation of the 2-substituted indoliz-

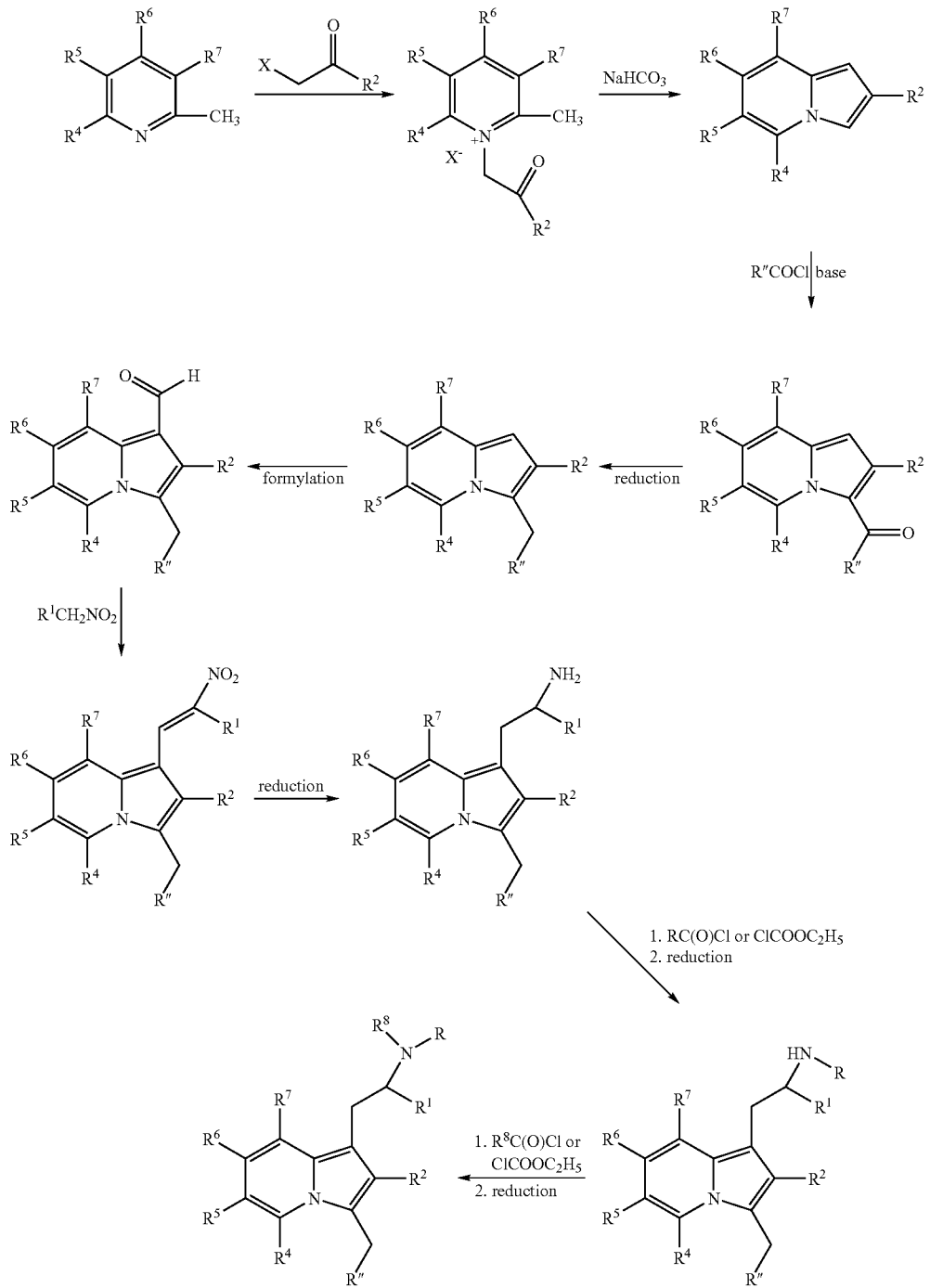

ine with an acid halide, such as acetyl chloride, or with an acid anhydride, such as acetic anhydride, with heating in excess reagent or in an organic solvent, such as dichloroethane, in the presence of a base, such as triethylamine (TEA) gives the 2-substituted, 3-acyl or aroyl intermediate which is reduced with a reducing agent, such as lithium aluminum hydride (LAH), to give the 2-substituted-3-methylenesubstituted indolizine intermediate. Formylation of this intermediate using a formylating agent, such as the Vilsmeir reagent, gives the corresponding 1-formyl intermediate which is treated with a substituted or unsubstituted nitroalkane, such as nitroethane, in the presence of an ammonium salt, such as ammonium acetate, at elevated temperatures (50° C.-100° C.) to give a nitroolefin intermediate which is reduced by a reducing agent, such as LAH, to give the products of this invention. Treating these products with additional acid halide or with ethyl chloroformate followed by reduction with a reducing agent, such as LAH, gives additional products of this invention. Repetition of the last two steps gives N,N-disubstituted aminoethyl compounds of this invention ($NRR_8$).

Compounds in which $R^3$ is hydrogen may be prepared, for example, according to Scheme 2. Variables are as described in Formula 1.

In Scheme 2, a substituted or unsubstituted 2-pyridinepropaneamide is dissolved in an organic solvent, such as acetone, with warming. A halomethylketone, such as bromoacetophenone, is added and the reaction mixture is heated at elevated temperature, such as the reflux temperature of the organic solvent, overnight. After standing at room temperature for 24-72 hours, the organic solvent is decanted and the residue is treated with a polar solvent, such as ethanol, and heated at elevated temperature, such as the reflux temperature of the organic solvent, for several hours. The organic solvent is removed under reduced pressure and the residue is recrystallized from an organic solvent, such as heptane to give the corresponding indolizine acetamide. Reduction of the acetamide with a reducing agent, such as LAH, in an organic solvent, such as ethyl ether, under an inert atmosphere, gives compounds of this invention where $R^3$ is hydrogen. Further compounds of this invention can be prepared by treating the aminoethylindolizines sequentially with an acid chloride, such as acetyl chloride, or with ethyl chloroformate followed by reduction of the carbonyl compound with a reducing agent such as LAH, to give N-substituted aminoethylindolizine

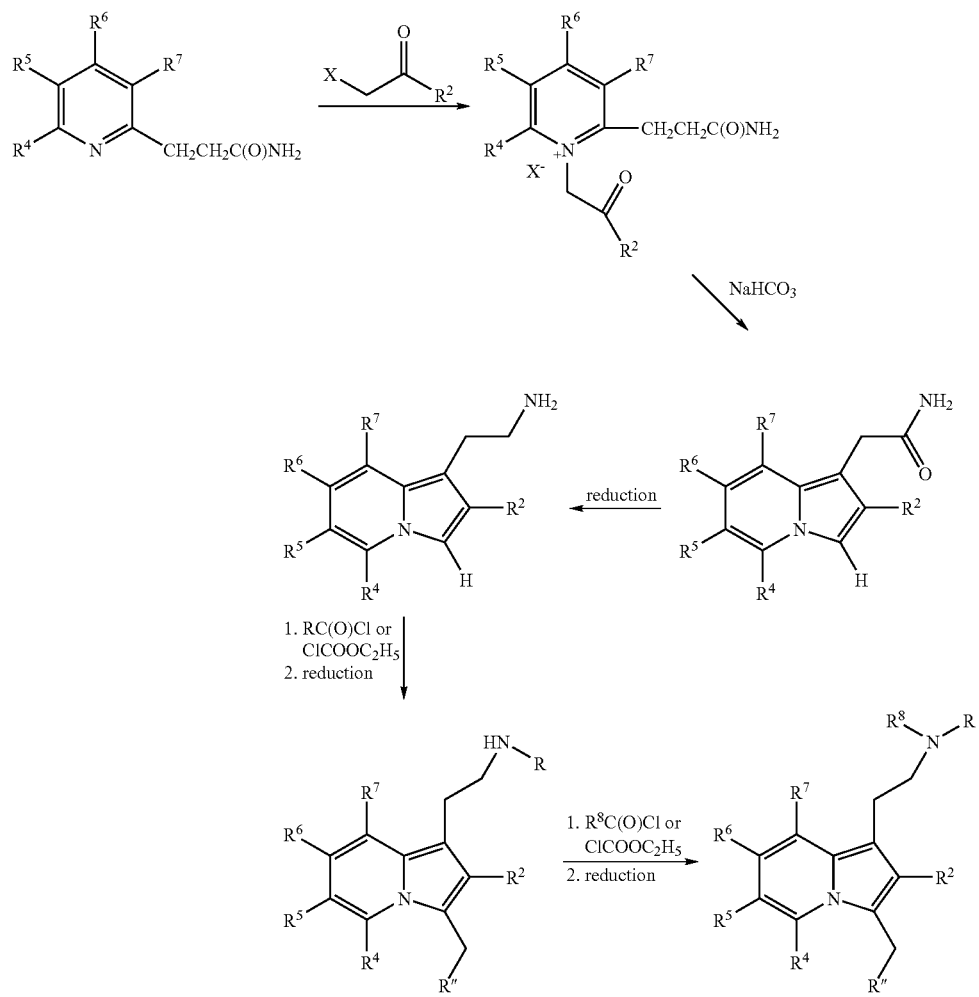

compounds of this invention. Repetition of the last two steps gives N,N-disubstituted aminoethylindolizine compounds of this invention.

Compounds in which $R^2$ and $R^3$ are taken together form a carbocyclic ring may be prepared, for example, according to Scheme 3. Variable "n" is 0, 1, 2 or 3. Remaining variables are as described in Formula 1.

anone, are heated at elevated temperature, such as 50° C. to 150° C., in an organic solvent, such as benzene, for 24-72 h. with removal of water, such as the use of a Dean-Stark trap, to give the indolizine ethyl ester in Scheme 3. The ester is hydrolyzed to the corresponding acid using a base, such as sodium ethoxide. The carboxylic acid is decarboxylated by heating in a high boiling solvent, such as bromobenzene, to

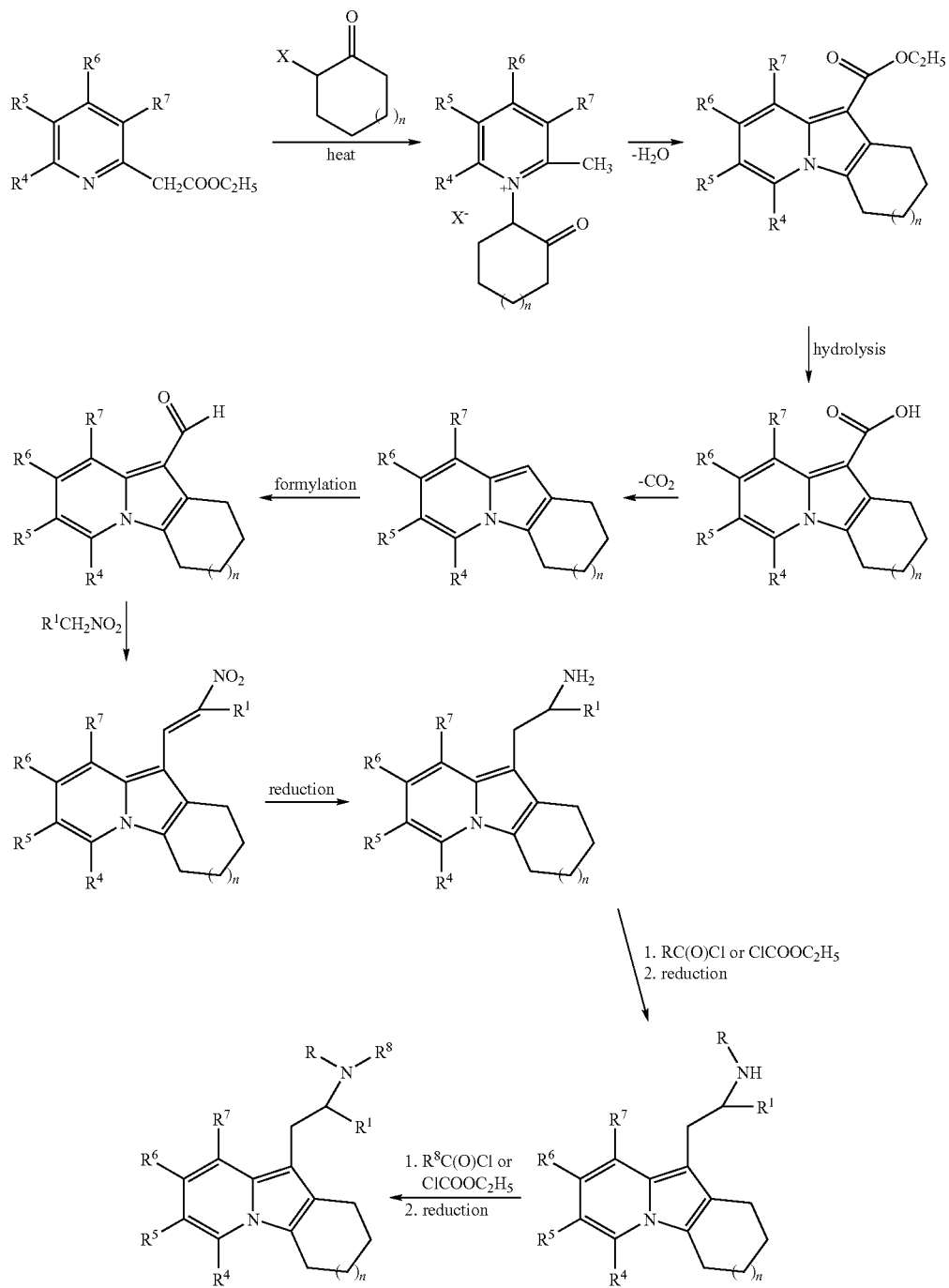

SCHEME 3

In Scheme 3, a substituted or unsubstituted -2-pyridylacetate and a 2-halocycloalkanone, such as 2-chlorocyclohexanone give the corresponding cycloalkylfused indolizine. Treatment of the cycloalkylfused indolizine with a formylating agent, such as the Vilsmeir reagent, gives the 10-formyl compound. Reaction of the 10-formyl compound with excess nitroalkane, such as nitroethane, in the presence of an ammonium salt, such as ammonium acetate, at elevated temperature, such as 50° C. to 150° C., gives the corresponding nitroolefin which is reduced to the corresponding aminoethyl compounds of this invention using a reducing agent, such as LAH. Additional compounds of this invention can be prepared by further treatment of the 10-aminoethylcycloalkylfused indolizine compounds with additional acid chloride or ethyl chloroformate followed by reduction of the carbonyl product with a reducing agent, such as LAH, to give 10-N-substituted aminoethylcycloalkylfused indolizines of this invention. Repetition of the last two steps gives N,N-disubstituted aminoethylindolizine compounds of this invention.

In certain embodiments, the invention relates to compositions comprising at least one compound of formula 1, or a pharmaceutically acceptable salt thereof, and one or more pharmaceutically acceptable carrier. Such compositions are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those carriers, excipients and diluents that are compatible with the other ingredients in the formulation and are biologically acceptable.

The compounds of formula 1 can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of formula 1 can be administered rectally or vaginally in the form of a conventional suppository. For administration by intranasal or intrabronchial inhalation or insufflation, the compounds of formula 1 can be formulated into an aqueous or partially aqueous solution, which can then be utilized in the form of an aerosol. The compounds of formula 1 can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount of compound of formula 1 provided to a patient will vary depending upon what is being administered, the purpose of the administration, such as prophylaxis or therapy, the state of the patient, the manner of administration, and the like. In therapeutic applications, compounds of formula 1 are provided to a patient suffering from a condition in an amount sufficient to treat or at least partially treat the symptoms of the condition and its complications. An amount adequate to accomplish this is an "effective amount" as described previously herein. The dosage to be used in the treatment of a specific case must be subjectively determined by the attending physician. The variables involved include the specific condition and the size, age, and response pattern of the patient. Generally, a starting dose is about 5 mg per day with gradual increase in the daily dose to about 150 mg per day, to provide the desired dosage level in the patient.

In certain embodiments, the present invention is directed to prodrugs of compounds of formula 1. The term "prodrug," as used herein, means a compound that is convertible in vivo by metabolic means (e.g. by hydrolysis) to a compound of formula 1. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews*, 8:1-38(1992), Bundgaard, *J. of Pharmaceutical Sci-*

EXAMPLES

The invention is further demonstrated in the following examples. The examples are for purposes of illustration and are not intended to limit the scope of the present invention.

Example 1

2-(2-phenylindolizin-1-yl)ethylamine

2-Pyridinepropaneamide (8.0 g, 53 mmol) was dissolved in warm acetone (500 mL). 2-Bromoacetophenone (12.0 g, 60 mmol) was added and the reaction mixture was heated under reflux overnight. After standing at room temperature for 2 days, the solvent was decanted from the tan precipitate, which was dissolved in ethanol and heated under reflux for 6 h. After standing overnight at ambient temperature, the ethanol was removed under reduced pressure to give a residue which was recrystallized from heptane (500 mL) to give 2-(2-phenyl-indolizin-1-yl)acetamide. 2-(2-Phenylindolizin-1-yl)acetamide (450 mg, 1.8 mmol) was suspended in ethyl ether. To the suspension was added lithium aluminum hydride (360 mg) and the reaction mixture was heated under reflux overnight under a nitrogen atmosphere. After cooling to room temperature, an aqueous solution of Rochelle salt was cautiously added with stirring until a solution was observed. The phases were separated and the aqueous phase was extracted 3 times with ether. The combined organic layers were extracted with 0.1 N HCl, and the aqueous layer was made basic with 2.5 N NaOH. The aqueous phase was extracted with methylene chloride three times and the organic phase was evaporated under reduced pressure to give crude product. The product was purified by chromatography on silica gel eluting with 5-11% methanol in methylene chloride containing 1% ammonium hydroxide. A 53% yield of the title compound was obtained, mp 212-214° C.

Example 2

2-(3-ethyl-2-phenylindolizin-1-yl)ethylamine 2-(2-Phenylindolizin-1-yl)acetamide (2.0 g, 8.0 mmol) was dissolved in acetic anhydride (150 mL) to which sodium acetate (1.1 g) was added. The reaction mixture was heated overnight in an oil bath (140° C.). After cooling, the acetic anhydride was removed by evaporation under reduced pressure. The residue was treated with 0.1 N NaOH and extracted into methylene chloride. Evaporation of the organic phase gave a dark residue which was purified by colum chromatography on silica gel eluting with 20-50% ethyl acetate in hexane. The product of this reaction was dissolved in ethyl ether (200 mL), treated with lithium aluminum hydride (430 mg) and stirred under reflux overnight under a nitrogen atmosphere. After cooling, aqueous Rochelle salt was added with stirring until a solution was observed. The phases were separated and the aqueous phase was extracted with ether and then made basic with 2.5 N NaOH and extracted with methylene chloride 3 times. Evaporation of the combined organic layers gave a residue which was purified by chromatography on silica gel eluting with 5-11% methanol in methylene chloride containing 1% ammonium hydroxide. The product (230 mg) was dissolved in ethanol and treated with 1 equivalent of fumaric acid dissolved in ethanol. The solution was evaporated to give a residue which was recrystallized with methyl ethyl ketone to give the fumaric acid salt of the product as a tan solid, mp. 173-176° C. MS [M+H]$^+$ 265 m/z; Microanalysis consistent for $C_{18}H_{20}N_2$+1.2 $C_4H_4O_4$.

Example 3

2-(2-phenyl-3-propylindolizin-1-yl)ethylamine 2-(2-Phenylindolizin-1-yl)acetamide (1.0 g, 40 mmol) was dissolved in dichloroethane (35 mL) containing triethylamine (0.65 mL). To the stirred solution was added propionyl chloride (0.70 mL). The reaction mixture was heated in an oil bath (70° C.) over the weekend. After cooling, the reaction mixture was diluted with methylene chloride and water. The phases were separated and the aqueous phase was extracted with methylene chloride 3 times. Evaporation of the combined organic layers gave a residue which was purified by column chromatography on silica gel eluting with 1.0-1.2% methanol in methylene chloride to give 115 mg of 1-cyanomethyl-3-propionyl-2-phenylindolizine. The cyanomethyl keto indolizine was reduced to the title compound with lithium aluminum hydride (150 mg) in ethyl ether under reflux in a nitrogen atmosphere overnight. After cooling the reaction mixture was quenched with Rochelle salt and stirred to give a solution. The phases were separated and the aqueous phase was extracted with ether and then made basic with 2.5 N NaOH. The crude product was extracted into methylene chloride and the solvent removed under reduced pressure to give a residue which was purified on silica gel eluting with 9% methanol in methylene chloride to give 70 mg of the free base of the title compound. The free base was dissolved in ethanol to which an ethanolic solution of 70 mg of fumaric acid was added. The solution was evaporated and the residue was recrystallized from methyl ethyl ketone to give the fumaric acid salt of the title compound, mp: 169-172° C.; MS [M+H]$^+$ 279 m/z; Microanalysis was consistent for $C_{19}H_{22}N_2$+ $C_4H_4O_4$+0.7 $H_2O$

Example 4

2-(2-ethylindolizin-1-yl)ethylamine

2-Pyridinepropaneamide (6.5 g, 43 mmol) was dissolved in warm acetone (500 mL). 1-Bromobutanone (10.0 g, 66 mmol) was added and the reaction mixture was heated under reflux for 48 hours. The reaction mixture was cooled in a freezer and the acetone was decanted from a light brown solid (12 g). The solid was dissolved in hot ethanol (450 mL). Solid $NaHCO_3$ (10 g) was added and the reaction mixture was heated under reflux with stirring for 6 h. The reaction mixture was filtered to remove NaBr and the filtrate was evaporated under reduced pressure to give a brown solid residue. The residue was extracted 4 times with boiling hexane (500 mL). Each time the solvent was decanted from the remaining solid and cooled in the freezer. A final extraction was with boiling heptane (500 mL). Collection of the cooled filtrates and drying of the collected solid gave 1.35 g of 2-(2-ethylindolizin-1-yl)acetamide. The 2-(2-ethylindolizin-1-yl)acetamide (440 mg) in ethyl ether (90 mL) was treated with lithium aluminum hydride (360 mg) and heated under reflux in a nitrogen atmosphere overnight. After cooling to room temperature, an aqueous solution of Rochelle salt was cautiously added with stirring until a solution was observed. The phases were separated and the aqueous phase was extracted 3 times with ether. The combined organic layers were extracted with 0.1 N HCl, and the aqueous layer was made basic with 2.5 N NaOH. The aqueous phase was extracted with methylene chloride 3 times and the organic phase was evaporated under reduced pressure to give 410 mg of product as a yellow brown oil. The product (170 mg, 0.90 mmol) was dissolved in ethanol and treated with fumaric acid (52 mg, 0.45 mmol). The title compound was obtained as a golden brown solid, mp: 170-175° C. dec. MS [M+H]$^+$ 189 m/z; microanalysis was consistent for $C_{12}H_{16}N_2+C_4H_4O_4$.

Example 5

2-(2,3-diethylindolizin-1-yl)ethylamine 2-(2-ethylindolizin-1-yl)acetamide (3.10 g, 15 mmol) was dissolved in acetic anhydride (200 mL) to which sodium acetate (2.3 g) was added. The reaction mixture was heated overnight in an oil bath (140° C.). After cooling, the acetic anhydride was removed by evaporation under reduced pressure. The residue was treated with 0.1 N NaOH and extracted into methylene chloride. Evaporation of the organic phase gave a dark residue which was purified by column chromatography on silica gel eluting with 20-40% ethyl acetate in hexane to give a mixture of 1-cyanomethyl-2-ethyl-3-acetyl-indolizine and N-acetyl-2-(3-acetyl-2-ethylindolizin-1-yl) acetamide. 1-Cyanomethyl-2-ethyl-3-acetylindolizine (300 mg, 1.3 mmol) isolated from this reaction mixture was dissolved in ethyl ether (100 mL), treated with lithium aluminum hydride (300 mg) and stirred under reflux overnight under a nitrogen atmosphere. After cooling, aqueous Rochelle salt was added with stirring until a solution was observed. The phases were separated and the aqueous phase was extracted with ether and then made basic with 2.5 N NaOH and extracted with methylene chloride 3 times. Evaporation of the combined organic layers gave a residue which was purified by chromatography on silica gel eluting with 4-9% methanol in methylene chloride containing 1% ammonium hydroxide. The product (140 mg) obtained as a brown oil was dissolved in ethanol and treated with 1 equivalent of fumaric acid dissolved in ethanol. The solution was evaporated to give a residue which was recrystallized with methyl ethyl ketone to give the fumaric acid salt of the product as a light brown solid, mp. 166-171° C. MS [M+H]$^+$ 217 m/z; Microanalysis consistent for $C_{14}H_{20}N_2+1.0\ C_4H_4O_4+0.40\ H_2O$.

Example 6

N-[2-(2,3-diethylindolizin-1-yl)ethyl]-N-ethylamine

N-acetyl-2-(3-acetyl-2-ethylindolizin-1-yl)acetamide (330 mg, 1.3 mmol) isolated in Example 5 was stirred in anhydrous ethyl ether (120 mL) to which lithium aluminum hydride (330 mg) was added. The reaction mixture was heated in a nitrogen atmosphere under reflux overnight. After cooling to room temperature, Rochelle salt was added with stirring until everything dissolved. The phases were separated and the aqueous phase was extracted with ether one time. Evaporation of the organic phase gave a residue, which was purified by flash column chromatography on silica gel eluting with 3-10% methanol in methylene chloride containing 1% ammonium hydroxide. The product (110 mg) was dissolved in ethanol, treated with a solution of fumaric acid (110 mg) dissolved in ethanol and evaporated to give a residue which was recrystallized from methyl ethyl ketone. The title compound was obtained as a greenish-tan solid, mp: 154-158° C. Mass spectrum: [M+H]$^+$ 245 m/z.

Example 7

2-(2-ethyl-3-propylindolizin-1-yl)ethylamine 2-(2-ethylindolizin-1-yl)acetamide (1.0 g, 5 mmol) was dissolved in dichloroethane (30 mL) to which was added triethylamine (TEA, 0.65 mL) N,N-dimethylaminopyridine (DMAP, 60 mg) and propionyl chloride (0.7 mL). The reaction mixture was heated under reflux in a $N_2$ atmosphere overnight. The cooled reaction mixture was partitioned between water and methylene chloride. The phases were separated and the aqueous phase was extracted with methylene chloride 3 times. The organic layers were combined and evaporated to give a residue which was purified by silica gel column chromatography eluting with ethyl acetate. A total of 600 mg of 2-(2-ethyl-3-propionylindolizin-1-yl)-acetamide was recovered. 2-(2-ethyl-3-propionylindolizin-1-yl)-acetamide (400 mg, 1.5 mmol) was suspended in anhydrous ethyl ether to which lithium aluminum hydride (LAH, 380 mg) was added. The suspension was heated under reflux in a $N_2$ atmosphere overnight. After cooling to room temperature the reaction mixture was partitioned between ether and aqueous Rochelle salt. After stirring for 1 h, the phases were separated. The aqueous phase was extracted with ether 2 times. Evaporation of the combined organic layers gave a residue which was purified on silica gel eluting with 1 L each of 5%, 10%, 12% methanol in methylene chloride containing 4 mL of conc. $NH_4OH$. The title compound was isolated (85 mg), dissolved in ethanol and treated with an ethanolic solution of fumaric acid (65 mg). The ethanol was evaporated and the residue was recrystallized from methyl ethyl ketone (MEK) to give the title compound as the fumaric acid salt, mp: 154-158° C.; Mass sSpectrum [M+H]$^+$ 231 m/z.

Example 8

N-[2(2-ethyl-3-propylindolizin-1-yl)ethyl-N-propylamine 2-(2-ethylindolizin-1-yl)acetamide (1.0 g, 5 mmol) was allowed to react with propionyl chloride (0.7 mL) as described in Example 7. After partial purification of the crude product on silica gel eluting with 10-50% ethyl acetate in hexane, a mixture of 1-cyanomethyl-2-ethyl-3-propionylindolizine I and N-acetyl-2-(3-propionyl-2-ethylindolizin-1-yl)acetamide II were collected (1.4 g). Reduction of this mixture with LAH and separation of the products by chromatography on silica gel eluting with 5-15% methanol in methylene chloride containing ammonium hydroxide gave the compound of Example 7 (570 mg) and the free base of the title compound (350 mg). The free base was dissolved in ethanol and treated with an ethanolic solution of fumaric acid (150 mg). Evaporation of the solvent gave a brown residue, which was recrystallized from MEK to give the fumaric acid salt of the title compound (375 mg). Mp: 136-138° C.

Example 9

2-(2-ethyl-3-propylindolizin-1-yl)-1-methylethylamine

2-Ethyl-3-propylindolizine (2.68 g, 14.3 mmol) was dissolved in dimethylformamide (DMF, 10 mL) and added to a solution of freshly distilled $POCl_3$ (1.4 mL) in DMF (10 mL).

After heating in an oil bath at 40° C. for 1 h, the mixture was allowed to cool and was carefully diluted with water (initial exotherm). The solid that precipitated was recovered by filtration and recrystallized from methanol and water to give the 1-formyl analog as an olive colored solid. Mp: 80-82° C. [M+H]$^+$ 216 m/z. The formyl compound (1.3 g) was dissolved in nitroethane (13 mL). Ammonium acetate (520 mg) was added and the reaction mixture was heated at 100° C. under a $N_2$ atmosphere for 1 h. After cooling, methanol was added and the reaction mixture was placed in a freezer for 24 h. Evaporation of the volatiles gave a residue which was purified by column chromatography on silica gel eluting with 10-15% ethyl acetate in hexane. A nitroolefin intermediate was isolated as a dark red solid (270 mg), mp: 63-66° C. [M+H]$^+$ 273 m/z. The nitroolefin above was combined with additional nitroolefin (1.65 g, 6 mmol) and reduced with LAH (1.9 g) in ether at room temperature under $N_2$ overnight. After quenching and workup as described in Example 1 the crude product was purified by column chromatography on silica gel eluting with 5-15% methanol in methylene chloride containing ammonium hydroxide to give the title compound (450 mg). The product was dissolved in ethanol and treated with an ethanolic solution of fumaric acid (209 mg, 1.8 mmol). Upon trituration a precipitate formed slowly. The solid was isolated by filtration and dried to give 270 mg of the title compound as the fumaric acid salt. Mp: 184-186° C. Mass spectrum: [M+H]$^+$ 245 m/z.

Example 10

1-(2-methyl-3-propylindolizin-1-yl)propan-2-amine

According to the procedure described in Example 9, 2-methyl-3-propylindolizine (400 mg) was converted to the title compound (75 mg). The title compound was converted to the fumaric acid salt, mp: 147-150° C.; Mass Spectrum [M+H]$^+$ 231 m/z.

Example 11

1-(2-methyl-3-propylindolizin-1-yl)butan-2-amine

According to the procedure in Example 9, 1-formyl-2-methyl-3-propylindolizine (570 mg, 2.8 mmol) and ammonium acetate (240 mg) in 1-nitropropane (12 mL) were heated at 100°C. with stirring for 3 h. Purification by column chromatography on silica gel eluting with 5-15% ethyl acetate in hexane gave the corresponding nitroolefin (270 mg) as a red solid, mp: 71-73° C. Reduction with LAH and workup as described in Example 9 gave the title compound, which was converted to the fumaric acid salt, mp: 183-185° C.

Example 12

2-(1,2,3,4-tetrahydropyrido[1,2-a]indol-10-yl)ethylamine

2-Pyridylacetate (25 g, 150 mmol) and 2-chlorocyclohexanone were heated under reflux in dry benzene for 42 h. under a Dean Stark trap to remove water. Evaporation of the volatiles under reduced pressure gave a very thick red-brown oily residue. The residue was treated with toluene and filtered. The toluene filtrate was evaporated to give an orange-brown oil. The oil was purified on alumina eluting with 10% petroleum ether in toluene to give 2.7 g of 1,2,3,4-tetrahydropyrido[1,2-a]indol-10-carboxylic acid ethyl ester [modification of L. K. Dalton; T. Teitei *Aust. J. Chem.* 1969 22, 1525-1530]. The ethyl ester (1 g, 4 mmol) was dissolved in ethanol (40 mL) with warming. To the solution was added 2.5 N NaOH (30 mL). The reaction mixture was heated under reflux for 2 h, then allowed to cool and stir at room temperature for 2 days. The solution was acidified with 2N HCl and extracted into methylene chloride. Removal of the volatiles under reduced pressure gave a residue, which was purified by column chromatography on silica gel eluting with 5-15% ethyl acetate in hexane. The corresponding carboxylic acid was obtained. The carboxylic acid (210 mg, 0.98 mmol) was dissolved in bromobenzene and heated at 170° C. for 15 min. The solvent was removed under reduced pressure to give a residue, which was purified on silica gel eluting with 100% hexane to remove bromobenzene followed by 5% ethyl acetate in hexane to isolate the product. Evaporation of the volatiles gave 1,2,3,4,-tetrahydropyrido[1,2-a]indole (140 mg), mp: 55-57° C. [M+H]$^+$ 172 m/z. 1,2,3,4,-tetrahydropyrido[1,2-a]indole was formylated, converted to the nitroolefin and reduced to the corresponding ethylamine as described in Example 9 to give the title compound. The title compound was dissolved in ethanol and treated with an ethanolic solution of fumaric acid. After standing in a freezer overnight crystals formed. The solution was decanted from the crystals which were rinsed with ethyl ether and dried under reduced pressure to give the fumaric acid salt of the title compound, mp: 166-172° C. The filtrate was diluted with ethyl ether and a second crop of crystals was recovered, mp: 169-172° C.

Alternate synthesis: 1,2,3,4,-tetrahydropyrido[1,2-a]indole in anhydrous THF was treated with 2M oxalyl chloride in methylene chloride at 0-5° C. After stirring for 1.5 h the reaction was quenched by cautious addition of ammonium hydroxide. The reaction mixture was allowed to come to room temperature and stir for 1 h. The mixture was partitioned between water and methylene chloride. The bright yellow organic phase was separated, dried and evaporated to give a yellow residue, which was reduced with 2M $BH_3$-dimethylsulfide complex in THF under reflux for 6 h to give the title compound.

Example 13

Determination of Binding Affinity and Agonist Activity of Compounds of Formula 1

The ability of the compounds of this invention to act as 5HT$_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

To evaluate high affinity for the 5-HT$_{2C}$ receptor, a Chinese Hamster Ovary (CHO) cell line transfected with the cDNA expressing the human 5-hydroxytryptamine-2C (h-5-HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10-25 microliter (μl) volumes. Bovine Serum Albumin (BSA) was used as the standard in the protein determination by the method of Lowry et al., (*J. Biol. Chem.*, 193:265 (1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1-2 mg per ml of suspension. The preparation membrane suspension (many times concentrated) was aliquoted in 1 ml volumes and stored at −70 C until used in subsequent binding experiments.

Binding measurements were performed in a 96 well microtiter plate format, in a total volume of 200 μl. To each well was added: 60 μl of incubation buffer made in 50 mM Tris.HCl buffer, pH 7.4 and containing 4 mM $CaCl_2$; 20 μl of [$^{125}$I] DOI (S.A., 2200 Ci/mmol, NEN Life Science).

The dissociation constant, KD of [$^{125}$I] DOI at the human serotonin 5-$HT_{2C}$ receptor was 0.4 nM by saturation binding with increasing concentrations of [$^{125}$I] DOI. The reaction was initiated by the final addition of 100.0 μl of tissue suspension containing 50 μg of receptor protein. Nonspecific binding is measured in the presence of 1 μM unlabeled DOI added in 20.0 μl volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 μl Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs. log concentration of test drug. Nonlinear regression analysis of data points yields both the $IC_{50}$ and the $K_i$ values of test compounds with 95% confidence limits. Alternatively, a linear regression line of decline of data points is plotted, from which the $IC_{50}$ value can be read off the curve and the $K_i$ value determined by solving the following equation:

$$K_i = \frac{IC_{50}}{1 + \frac{L}{KD}}$$

where L is the concentration of the radioactive ligand used and the KD is the dissociation constant of the ligand for the receptor, both expressed in nM.

The following $K_i$'s (95% confidence interval) are provided for various reference compounds:

| Compound | $K_i$ |
|---|---|
| Ritanserin | 2.0 (1.3-3.1) nM |
| Ketanserin | 94.8 (70.7-127.0) nM |
| Mianserin | 2.7 (1.9-3.8) nM |
| Clozapine | 23.2 (16.0-34.0) nM |

-continued

| Compound | $K_i$ |
|---|---|
| Methiothepin | 4.6 (4.0-6.0) nM |
| Methysergide | 6.3 (4.6-8.6) nM |
| Loxapine | 33.0 (24.0-47.0) nM |
| mCPP | 6.5 (4.8-9.0) nM |
| DOI | 6.2 (4.9-8.0) nM |

The ability of the compounds of the invention to produce an agonist response at brain 5-$HT_{2C}$ was assessed by determining their effect on calcium mobilization using the following procedure: CHO cells stably expressing the human 5-$HT_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hours prior to the evaluation of 5-$HT_{2C}$ receptor-stimulated calcium mobilization. For calcium studies cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510-560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT and $EC_{50}$ values were estimated by non-linear regression analysis of the log-concentration % maximum 5-HT response curves using the 4-parameter logistic function.

The following $EC_{50}$'s and $IC_{50}$'s are provided for various reference compounds:

| 5-HT | $EC_{50}$ | 0.5 nM |
|---|---|---|
| DOI | $EC_{50}$ | 0.5 nM |
| mCPP | $EC_{50}$ | 5.4 nM |

The results of the standard experimental test procedures described in the preceding paragraphs were as follows:

| | 5-$HT_{2C}$ Affinity | 5-$HT_{2C}$ Function | |
|---|---|---|---|
| Compound | $K_i$ (nM) | $EC_{50}$ (nM) | Emax (%) |
| Example 1 | 272 | | |
| Example 2 | 117 | | |
| Example 3 | 54 | | |
| Example 4 | 121 | | |
| Example 5 | 35 | 11 | 80 |
| Example 6 | 228 | | |
| Example 7 | 21 | 19 | 100 |
| Example 8 | 208 | | |
| Example 9 | 124 | | |
| Example 10 | 17 | 46 | 90 |

-continued

| Compound | 5-HT$_{2C}$ Affinity K$_i$ (nM) | 5-HT$_{2C}$ Function EC$_{50}$ (nM) | Emax (%) |
|---|---|---|---|
| Example 11 | 457 | | |
| Example 12 | 98 | | |

The compounds of this invention thus have affinity for and agonist or partial agonist activity at brain serotonin 5HT$_{2C}$ receptors. They are therefore of interest for the treatment of the central nervous system conditions described previously herein.

When ranges are used herein for physical properties, such as molecular weight, or chemical properties, such as chemical formulae, all combinations and subcombinations of ranges and specific embodiments therein are intended to be included.

The entire disclosure of each patent, patent application, and publication cited or described in this document is hereby incorporated by reference.

Those skilled in the art will appreciate that numerous changes and modifications can be made to the preferred embodiments of the invention and that such changes and modifications cam be made without departing from the spirit of the invention. It is, therefore, intended that the appended claims cover all such equivalent variations as fall within the true spirit and scope of the invention.

What is claimed:

1. A compound of formula (1):

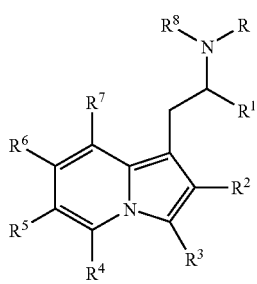

or a pharmaceutically acceptable salt thereof;
wherein
R is H, C$_1$-C$_6$ alkyl, C$_6$-C$_{10}$ aryl, 5 to 10 membered heteroaryl having 1 to 3 heteroatoms each independently selected from nitrogen, oxygen and sulfur, or —C(O)R', wherein R' is C$_1$-C$_6$ alkyl, C$_6$-C$_{10}$ aryl, or 5 to 10 membered heteroaryl having 1 to 3 heteroatoms each independently selected from nitrogen, oxygen and sulfur;
R$^1$ is H, C$_1$-C$_6$ alkyl, C$_3$-C$_8$ cycloalkyl, or C$_1$-C$_6$ fluoroalkyl;
R$^2$ is C$_1$-C$_6$ alkyl, C$_3$-C$_8$ cycloalkyl, C$_1$-C$_6$ fluoroalkyl, C$_6$-C$_{10}$ aryl, or 5 to 10 membered heteroaryl having 1 to 3 heteroatoms each independently selected from nitrogen, oxygen and sulfur;
R$^3$ is C$_3$-C$_6$ alkyl, C$_1$-C$_6$ alkyl-C$_3$-C$_8$ cycloalkyl, or C$_1$-C$_6$ fluoroalkyl;
or alternatively R$^2$ and R$^3$ can be taken together with the carbon atoms to which they are attached to form a ring of 5-8 carbon atoms;
R$^4$, R$^5$, R$^6$, and R$^7$ are each independently H, halogen, cyano, hydroxyl, carboxyl, C$_1$-C$_6$ alkyl, C$_1$-C$_6$ fluoroalkyl, C$_1$-C$_6$ alkoxy, C$_1$-C$_6$ fluoroalkoxy, C$_6$-C$_{10}$ aryl, C$_6$-C$_{10}$ aryloxy, 5 to 10 membered heteroaryl having 1 to 3 heteroatoms each independently selected from nitrogen, oxygen and sulfur, C$_2$-C$_8$ alkenyl, C$_2$-C$_6$ alkanoyl, C$_2$-C$_6$ alkanoyloxy, C$_2$-C$_6$ alkoxycarbonyl, carboxamido, C$_2$-C$_6$ alkanamido, C$_1$-C$_6$ alkanesulfonamido, amino, C$_1$-C$_6$ monoalkylamino, dialkylamino of 1 to 6 carbon atoms per alkyl moiety, C$_3$-C$_8$ cycloalkyl, or a 3 to 8 membered heterocycloalkyl having 1 to 3 heteroatoms each independently selected from nitrogen, oxygen and sulfur;
R$^8$ is H, C$_1$-C$_6$ alkyl, C$_3$-C$_8$ cycloalkyl, or C$_6$-C$_{10}$ aryl;
wherein any cycloalkyl or heterocycloalkyl group is saturated or partially saturated, and any aryl, heteroaryl, cycloalkyl, or heterocycloalkyl group may optionally be substituted with 1 to 5 substituents independently selected from halogen, hydroxyl, C$_1$-C$_6$ alkyl, C$_1$-C$_6$ fluoroalkyl, C$_1$-C$_6$ alkoxy, and C$_1$-C$_6$ fluoroalkoxy.

2. A compound of claim 1 wherein R is selected from H and C$_1$-C$_6$ alkyl.

3. A compound of claim 1 wherein R$^1$ is selected from H and C$_1$-C$_6$ alkyl.

4. A compound of claim 2 wherein R$^1$ is selected from H and C$_1$-C$_6$ alkyl.

5. A compound of claim 1 wherein R$^2$ is selected from optionally substituted phenyl and C$_1$-C$_6$ alkyl.

6. A compound of claim 1 wherein R$^3$ is C$_3$-C$_6$ alkyl.

7. A compound of claim 4 wherein R$^3$ is C$_3$-C$_6$ alkyl.

8. A compound of claim 5 wherein R$^3$ is C$_3$-C$_6$ alkyl.

9. A compound of claim 1 wherein R and R$^1$ are each independently selected from H and C$_1$-C$_6$ alkyl, R$^2$ is selected from optionally substituted phenyl and C$_1$-C$_6$ alkyl, and R$^3$ is C$_3$-C$_6$ alkyl.

10. A compound of claim 1 wherein R$^2$ and R$^3$ are taken together to form a ring of 5-8 carbon atoms.

11. A compound of claim 4 wherein R$^2$ and R$^3$ are taken together to form a ring of 5-8 carbon atoms.

12. A compound of claim 1 wherein R$^4$, R$^5$, R$^6$, and R$^7$ are each independently selected from H, halogen, C$_1$-C$_6$ alkyl, C$_1$-C$_3$ fluoroalkyl, C$_1$-C$_3$ alkoxy, and C$_2$-C$_8$ alkenyl.

13. A compound of claim 12 wherein R$^4$, R$^5$, R$^6$, and R$^7$ are each independently selected from H, halogen, and C$_1$-C$_6$ alkyl.

14. A compound of claim 13, wherein R$^4$, R$^5$, R$^6$, and R$^7$ are each H.

15. A compound of any one of claims 4 to 10 wherein R$^4$, R$^5$, R$^6$, and R$^7$ are each H.

16. A compound of claim 1 wherein R$^8$ is selected from H and C$_1$-C$_6$ alkyl.

17. A compound of claim 1 wherein R$^8$ is H.

18. A compound of claim 15 wherein R$^8$ is H.

19. A compound of claim 1 which is:
2-(3-ethyl-2-phenylindolizin-1-yl)ethylamine;
2-(2-phenyl-3-propylindolizin-1-yl)ethylamine;
2-(2,3-diethylindolizin-1-yl)ethylamine;
N-[2-(2,3-diethylindolizin-1-yl)ethyl]-N-ethylamine;
2-(2-ethyl-3-propylindolizin-1-yl)ethylamine;
N-[2-(2-ethyl-3-propylindolizin-1-yl)ethyl]-N-propylamine;
2-(2-ethyl-3-propylindolizin-1-yl)-1-methylethylamine;
1-(2-methyl-3-propylindolizin-1-yl)propan-2-amine;
1-(2-methyl-3-propylindolizin-1-yl)butan-2-amine; or
2-(1,2,3,4-tetrahydropyrido[1,2-a]indol-10-yl)ethylamine; or
a pharmaceutically acceptable salt thereof.

20. A pharmaceutical composition comprising a compound of claim 1 or a pharmaceutically acceptable salt thereof and one or more pharmaceutically acceptable carriers.

21. A compound which is 2-(2-phenylindolizin-1-yl)ethylamine or 2-(2-ethylindolizin-1yl)ethylamine.

* * * * *